(12) United States Patent
Theis et al.

(10) Patent No.: US 6,397,599 B1
(45) Date of Patent: Jun. 4, 2002

(54) METHOD FOR PRODUCING ETHYLENE OXIDE BY DIRECTLY OXIDIZING ETHYLENE WITH AIR OR OXYGEN

(75) Inventors: Gerhard Theis, Maxdorf (DE); Frans Vansant, Kalmthout (BE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/762,797
(22) PCT Filed: Sep. 20, 1999
(86) PCT No.: PCT/EP99/06941
§ 371 (c)(1),
(2), (4) Date: Feb. 13, 2001
(87) PCT Pub. No.: WO00/17177
PCT Pub. Date: Mar. 30, 2000

(51) Int. Cl.[7] ............................................. F01K 25/06
(52) U.S. Cl. ........................... 60/649; 60/651; 60/671
(58) Field of Search ......................... 60/649, 651, 671, 60/39.02, 39.182, 39.23, 648, 655

(56) References Cited

U.S. PATENT DOCUMENTS 3,552,122 A    1/1971  Parmegiani et al. ........... 60/39
4,074,981 A  * 2/1978  Slater ........................ 60/39.02
4,099,383 A  * 7/1978  Paull et al. .................... 60/648
4,121,912 A  * 10/1978 Barber et al. ............... 60/39.02

FOREIGN PATENT DOCUMENTS

DE    39 35 030     4/1991
EP    0 532 325     3/1993
JP    75007574      3/1975

OTHER PUBLICATIONS

Ullmann's Encyclopedia of Industrial Chemistry, 5th Edition, vol. A 10 pp. 117–133.

* cited by examiner

Primary Examiner—Hoang Nguyen
(74) Attorney, Agent, or Firm—Keil & Weinkauf

(57) ABSTRACT

In the preparation of ethylene oxide by direct oxidation of ethylene with air or oxygen using water as heat carrier to dissipate the heat of reaction, with water vapor being formed, a process for optimizing the specific energy consumption is proposed. In this, the water vapor is first expanded in one or more backpressure steam turbine(s) T for operating working machines M, before it is fed to one or more consumers, such as bottoms reboilers or steam injectors, for further utilization.

8 Claims, 3 Drawing Sheets

METHOD FOR PRODUCING ETHYLENE OXIDE BY DIRECTLY OXIDIZING ETHYLENE WITH AIR OR OXYGEN

The invention relates to a process for preparing ethylene oxide (called EO hereinafter) by direct oxidation of ethylene and to a process according to which glycol is produced from EO by hydrolysis, pressure dehydration, vacuum dehydration and subsequent distillation.

Currently, EO is prepared industrially by direct oxidation of ethylene with air or oxygen in the presence of silver catalysts. The reaction is highly exothermic (overall heat production from 225 to 400 kJ per mole of ethylene); therefore, to dissipate the excess heat of reaction, conventionally tube-in-shell reactors are employed, the reaction mixture being conducted through the tubes and a boiling liquid, for example kerosene or tetralin, recently frequently water, being circulated as heat carrier between the tubes. The present invention relates to processes according to which water is used as heat carrier.

Processes of this type are described, for example, in Ullmanns Encyclopedia of Industrial Chemistry, Fifth edition, Vol. A 10, pages 117ff. According to this, ethylene and oxygen are charged into a circulating gas stream which, in addition to the reactants, comprises inert gases and the byproduct of total oxidation of ethylene, carbon dioxide.

The water vapor produced in the direct oxidation of ethylene is, in the known process, generally expanded via a valve to the pressure of a steam grid. In the course of this, the energy content of the water vapor from the expansion is not utilized.

A significant proportion of ethylene oxide (EO) of the worldwide production is increasingly further processed to monoethylene glycol. To improve the selectivity of the EO hydrolysis, the hydrolysis reactor is operated with a high water excess (weight ratio of water: EO to 15:1). As a result, the proportion of higher glycols, in particular of diethylene glycol, triethylene glycol etc., can be forced down. The hydrolysis reactor is customarily operated at temperatures from 120° C. to 250° C. and pressures of 30–40 bar. The hydrolysis product is firstly dehydrated to a residual water content of 100–200 ppm and then fractionated into the various glycols in pure form.

The dehydration is generally performed in a cascade of pressure-staggered towers with decreasing pressure. For reasons of thermal integration, generally only the bottoms reboiler of the first pressure tower is heated with fresh steam, all further pressure towers in contrast are heated with the vapors of the respective preceding tower. Depending on water content of the hydrolysis reactor discharge and the pressure/temperature level of the external steam used in the bottoms reboiler of the first tower, the pressure dehydration cascade consists of from 2 to 7 towers. The pressure dehydration is followed by a vacuum dehydration. The dehydrated glycol-containing solution is fractionated in a plurality of towers into the pure substances monoethylene glycol, di- and triethylene glycol. It is an object of the present invention to utilize energetically, to the optimum extent, the water vapor produced in the direct oxidation of ethylene oxide with use of water as heat carrier and to improve the economic efficiency of the process for preparing EO and/or monoethylene glycol.

We have found that this object is achieved by a process for preparing EO by direct oxidation of ethylene with air or oxygen using water as heat carrier, with water vapor being formed which is then expanded. The invention comprises carrying out the expansion of the water vapor in one or more backpressure steam turbine(s).

Steam turbines describe in a known manner heat engines having rotating moving parts in which the pressure drop of constantly flowing steam is converted into mechanical work in one or more stages. Depending on the type of steam removal, various types of steam turbines are differentiated; in what are termed the backpressure steam turbines, the exhaust steam energy is further exploited for other purposes, generally for heating.

For the use in the present process, in principle any backpressure steam turbine can be used.

Steam turbines are generally operated with steam feed under constant conditions. In contrast thereto, according to the invention a steam turbine is operated with continuously increasing steam rate and rising steam pressure. The conditions (steam rate, pressure) in the time average are critical for economic efficiency of this solution.

The industrial catalysts used in the ethylene oxidation, which generally comprise up to 15% by weight of silver in the form of a finely particulate layer on a support, lose activity with increasing operating time, and the selectivity of the partial oxidation of ethylene oxide decreases. In order to keep the production rate of an EO plant constant with increasing operating time, the reaction temperature must be increased with the same conversion rate, as a result of which the pressure of the resulting water vapor increases. The simultaneous decreasing selectivity leads to greater steam rates. In the case of conventional industrial plants, frequently at the start of operation a water vapor pressure in the range of 30 bar arises, and with continuous increase over an operating time of 2 years to a value of about 65 bar.

Depending on the energy available, the steam turbine(s) can drive one or more working machines, in particular process pumps (to transport circulating water) or compressors (for gaseous process streams) and/or one or more generators. Water vapor fed to the steam turbine(s) generally has a pressure from 25 to 70 bar, preferably from 30 to 65 bar.

In a particularly preferred process variant, the water vapor arising in the direct oxidation of ethylene in a process for producing monoethylene glycol from ethylene oxide by hydrolysis, pressure dehydration, vacuum dehydration and subsequent distillation is expanded via the steam turbine(s) to the pressure of the bottoms reboiler of the pressure dehydration tower or of the bottoms reboiler of the first pressure dehydration tower of a cascade and the exhaust steam of the steam turbine(s) is used for heating the pressure dehydration tower or the first pressure dehydration tower of the cascade.

By means of an appropriate design of the glycol pressure dehydration stages, the steam rate required for the pressure dehydration can be approximated to the steam rate generated in the direct oxidation of ethylene. This significantly reduces the external consumption of high-pressure steam in the time average.

The pressure dehydration tower or the first pressure dehydration tower of the cascade is heated via a bottoms reboiler and the condensate is recycled to the EO reaction stage.

According to further embodiments, the expansion via the steam turbine(s) is carried out to the pressure of a steam grid or to the operating pressure of consumers, such as steam injectors or bottoms reboilers.

By means of the process of the invention, the specific energy consumption of an EO and/or monoethylene glycol plant can be decreased by a high degree of thermal integration. The towers in the glycol process can be operated predominantly with contaminated steam from the pressure dehydration. An external supply of high-pressure steam is significantly reduced in the time average.

The economically and energetically most favorable solution depends on the site boundary conditions, in particular the level of the steam grids and the energy costs.

The invention is described below in more detail with reference to a drawing and examples.

The stream data in the examples below apply to the average of an operating period of the catalyst in the EO reaction.

Figure 1:
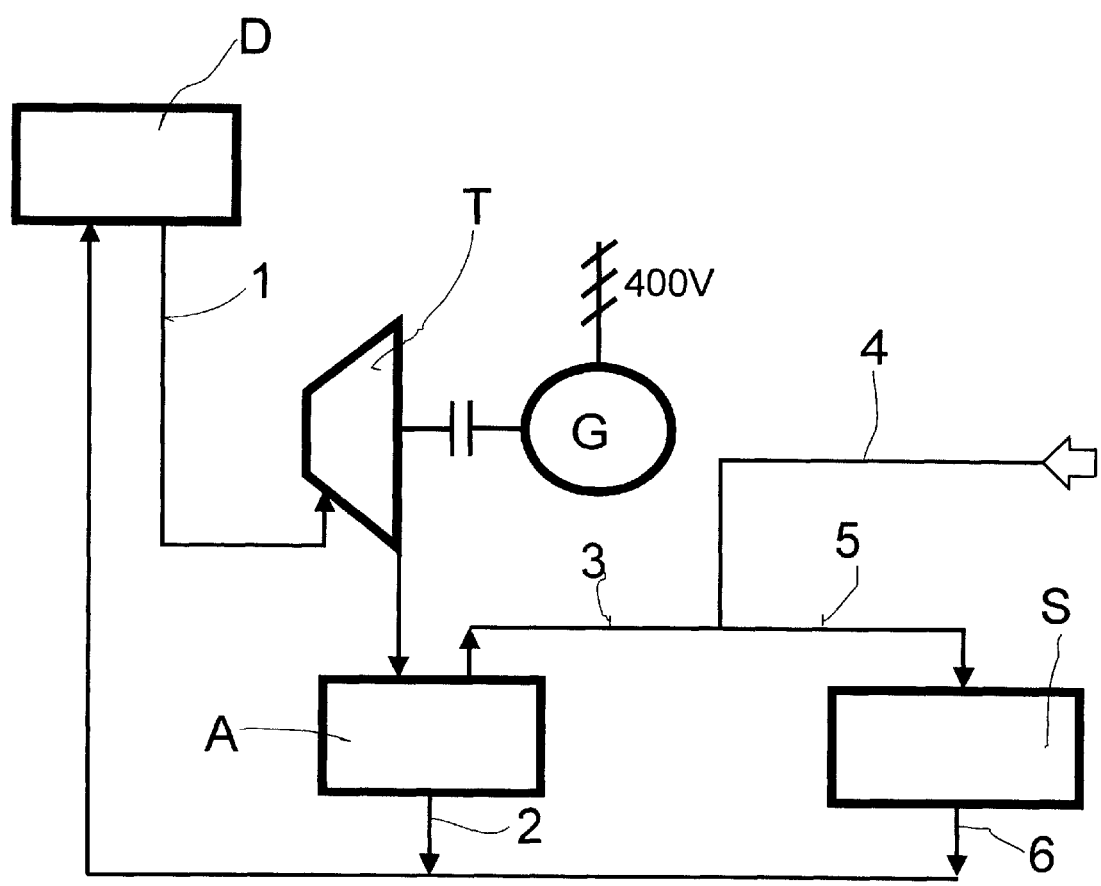
FIG. 1 is a diagrammatic illustration of one example of the multiple utilization of the steam recovered from the ethylene oxide reaction process of this invention.

FIG. 1 shows diagrammatically an example of the multiple utilization of steam from the EO reaction in a backpressure steam turbine with attached generator and expansion to the backpressure of the bottoms reboiler of the $1^{st}$ stage of the glycol pressure dehydration. The stream data are listed in Table 1. The saturated steam 1 taken off from the steam drum D of the EO reactor is expanded in a backpressure steam turbine T to a pressure of 21 bar absolute. The turbine T drives a generator G for electricity generation (e.g. 400 V). Depending on the efficiency of the turbine T, the drive power is approximately 2 MW. The expansion in the turbine T takes place in the wet steam area, for which reason in a separator A condensate 2 and saturated steam 3 are separated. The condensate 2 is pumped back to the steam drum D. The saturated steam 3 is fed to the bottoms reboiler S of the $1^{st}$ stage of the glycol pressure dehydration. In the event of an inadequate rate, the saturated steam 3 is supplemented with grid steam 4. The condensate 6 flowing out from the bottoms reboiler S is likewise pumped back to the steam drum D.

Figure 2:
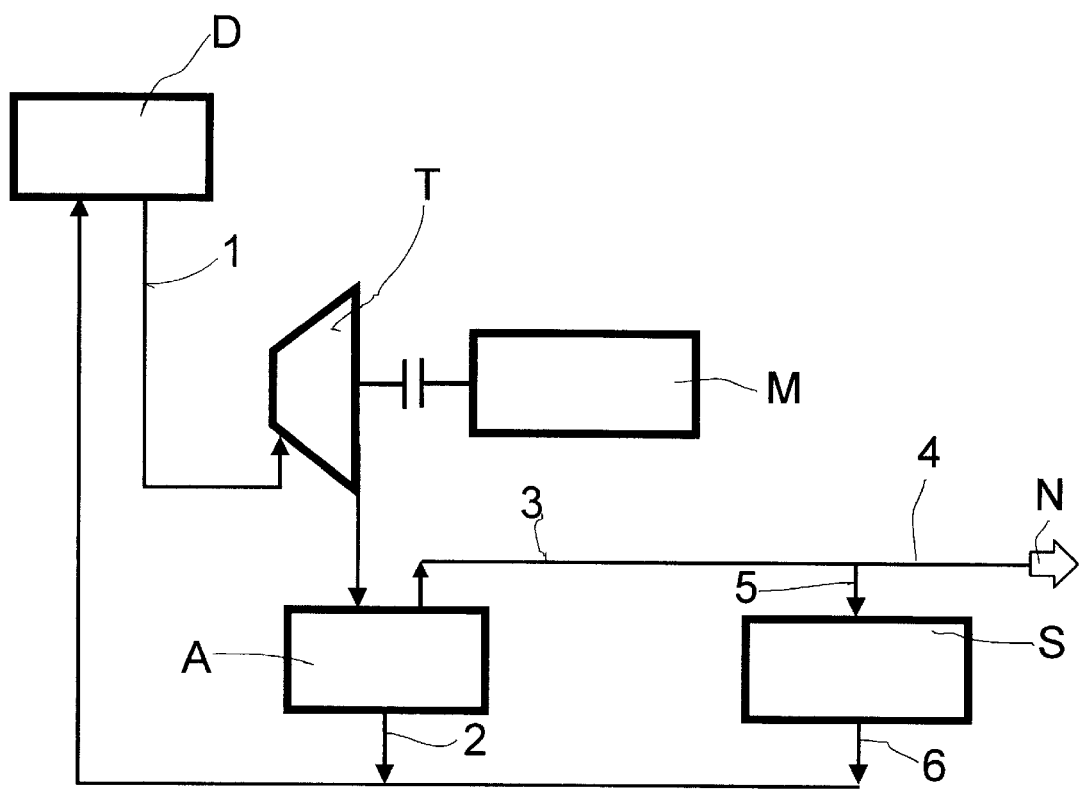
FIG. 2 is a diagrammatic representation of a second example of the multiple utilization of the steam recovered from the ethylene oxide reaction process of this invention.

FIG. 2 shows a second example. Here, the expansion is carried out to a backpressure of 5 bar absolute (for stream data see Table 2). By means of the steam turbine T, one or more working machines M (process pumps, compressors) can be driven at a power of approximately 2.7 MW. The saturated steam is fed for the most part to the bottoms reboiler S of a tower (stream 5). The remaining saturated steam 4 is discharged to the steam grid N.

Figure 3:
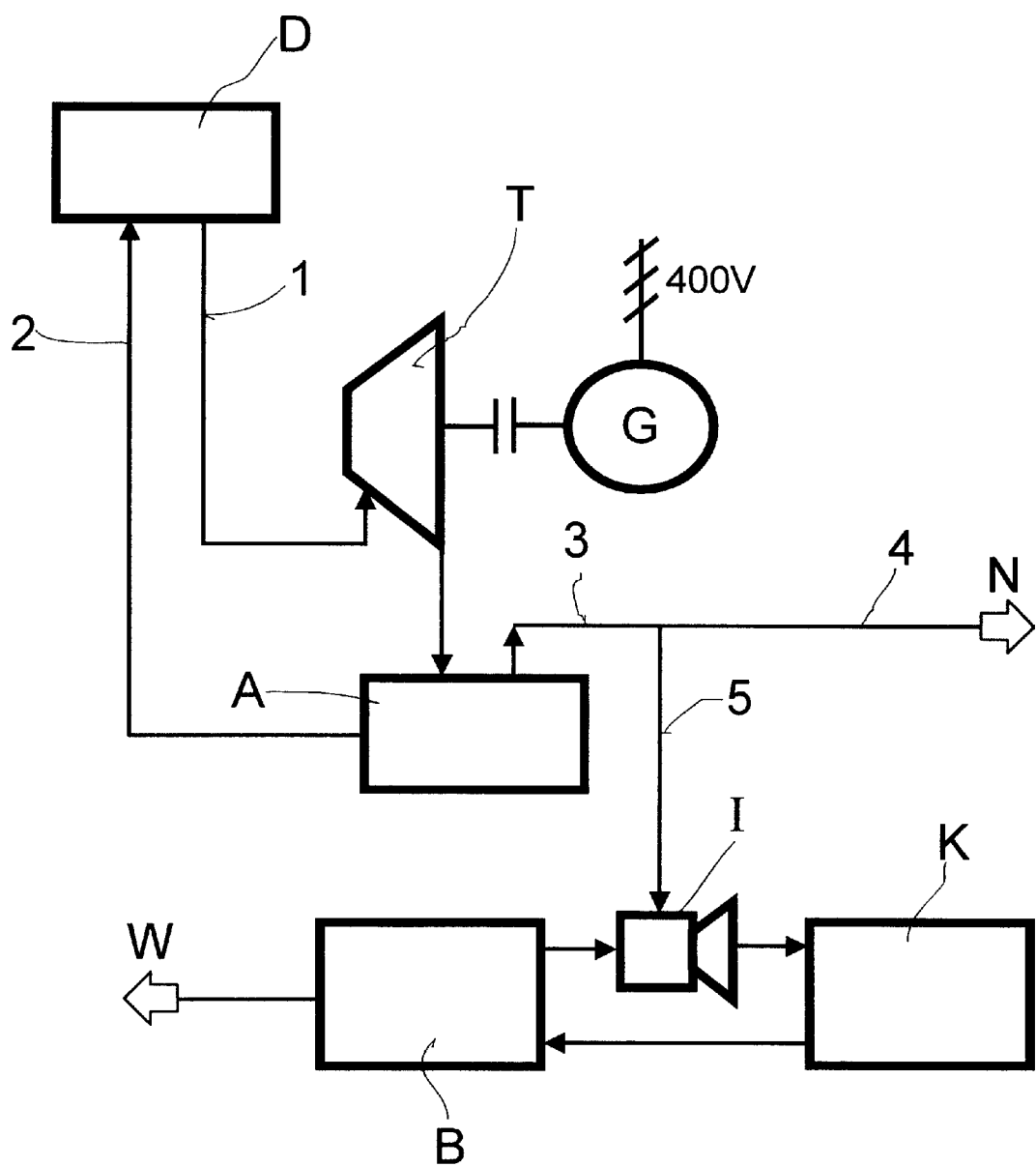
FIG. 3 is a diagrammatic representation of a third example of the multiple utilization of the steam recovered from the ethylene oxide reaction process of this invention.

FIG. 3 shows a third example. The expansion is carried out to a backpressure of 17 bar absolute (for stream data see Table 3). The steam turbine T drives a generator G for electricity generation (eg. 400 V) at a power of approximately 3.8 MW. The saturated steam 3 is for the most part discharged into the steam grid N (stream 4). The partial stream 5 operates one or more steam injectors I. In the example shown, using the injectors, the bottom of a tower K is heated and at the same time the effluent bottoms stream is cooled by generating reduced pressure in a downstream vessel B (evaporative cooling). The condensate is fed in this case to the process water W.

TABLE 1

| Stream No. 1 | | 1 | 2 | 3 | 4 | 5 | 6 |
|---|---|---|---|---|---|---|---|
| Total stream | t/h | 52.3 | 2.6 | 49.7 | 9.3 | 59 | 59 |
| Pressure | bar$_{abs}$ | 53 | 21 | 21 | 41 | 21 | |

TABLE 1-continued

| Stream No. 1 | | 1 | 2 | 3 | 4 | 5 | 6 |
|---|---|---|---|---|---|---|---|
| Temperature | °C. | 268 | 215 | 215 | 400 | 242 | 215 |
| | | g | l | g | g | g | l | g: gaseous
l: liquid

TABLE 2

| Stream No. 1 | | 1 | 2 | 3 | 4 | 5 | 6 |
|---|---|---|---|---|---|---|---|
| Total stream | t/h | 31.4 | 2.8 | 28.6 | 12.6 | 16 | 16 |
| Pressure | bar$_{abs}$ | 53 | 5 | 5 | 5 | 5 | 5 |
| Temperature | °C. | 268 | 152 | 152 | 152 | 152 | 152 |
| | | g | l | g | g | g | | g: gaseous
l: liquid

TABLE 3

| Stream No. 1 | | 1 | 2 | 3 | 4 | 5 | 6 |
|---|---|---|---|---|---|---|---|
| Total stream | t/h | 83.7 | 4.8 | 78.9 | 63.4 | 15.5 | |
| Pressure | bar$_{abs}$ | 53 | 17 | 17 | 17 | 17 | |
| Temperature | °C. | 268 | 204 | 204 | 204 | 204 | |
| | | g | l | g | g | g | | g: gaseous
l: liquid

We claim:

1. A process for preparing ethylene oxide by direct oxidation of ethylene with air or oxygen using water as heat carrier to dissipate the heat of reaction, wherein water vapor is formed with continuously increasing pressure over the operating time of said process, which water vapor is then expanded, which comprises carrying out the expansion of the water vapor in one or more backpressure steam turbine(s) (T).

2. A process as claimed in claim 1, wherein the steam turbine(s) (T) drives (drive) one or more working machines (M).

3. A process as claimed in claim 1, wherein the water vapor fed to the steam turbine(s) (T) has a pressure from 25 to 70 bar.

4. A process as claimed in claim 1, according to which monoethylene glycol is produced from ethylene oxide by hydrolysis, pressure dehydration, vacuum dehydration and subsequent distillation, and the water vapor arising in the direct oxidation of ethylene is expanded via the steam turbine(s) (T) to the pressure of the bottoms reboiler (S) of the pressure dehydration tower or of the bottoms reboiler (S) of the first pressure dehydration tower of a cascade, and wherein the exhaust steam of the steam turbine(s) (T) is used for heating the pressure dehydration tower or the first pressure dehydration tower of the cascade.

5. A process as claimed in claim 1, wherein the expansion is carried out via the steam turbine(s) (T) to the pressure of a steam grid (N), or to the operating pressure of other energy consumers.

6. A process as claimed in claim 2, wherein said working machines (M) are selected from the group consisting of process pumps, compressors and generators (G).

7. A process as claimed in claim 3, wherein said pressure is from 30 to 65 bar.

8. A process as claimed in claim 5, wherein said other energy consumers are steam injectors or bottoms reboilers.

* * * * *